(12) United States Patent
Bashkansky et al.

(10) Patent No.: US 12,318,157 B2
(45) Date of Patent: Jun. 3, 2025

(54) MULTIPLE END EFFECTOR INTERFACES COUPLED WITH DIFFERENT KINEMATICS

(71) Applicant: Mazor Robotics Ltd., Caesarea (IL)

(72) Inventors: Boris Bashkansky, Atzmon-Segev (IL); Ori Ben Zeev, Ramat HaSharon (IL); Adi Sandelson, Givatayim (IL); Gillan M. Grimberg, Tel Aviv-Jaffa (IL)

(73) Assignee: Mazor Robotics Ltd., Caesarea (IL)

( * ) Notice: Subject to any disclaimer, the term of this patent is extended or adjusted under 35 U.S.C. 154(b) by 713 days.

(21) Appl. No.: 17/534,089

(22) Filed: Nov. 23, 2021

(65) Prior Publication Data
US 2023/0157774 A1    May 25, 2023

(51) Int. Cl.
*A61B 34/32* (2016.01)
*B25J 15/04* (2006.01)

(52) U.S. Cl.
CPC ............... *A61B 34/32* (2016.02); *B25J 15/04* (2013.01); *G05B 2219/39* (2013.01); *G05B 2219/39253* (2013.01); *G05B 2219/39466* (2013.01)

(58) Field of Classification Search
CPC ......... A61B 34/30; A61B 34/32; A61B 34/37; A61B 2034/305; B25J 15/04; G05B 2219/39; G05B 2219/39253; G05B 2219/39466
See application file for complete search history.

(56) References Cited

U.S. PATENT DOCUMENTS

| | | | | |
|---|---|---|---|---|
| 4,830,569 | A | * | 5/1989 | Jannborg ............. B25J 19/0041 901/41 |
| 5,974,643 | A | * | 11/1999 | Hays ....................... B25J 15/04 901/41 |
| 9,630,315 | B2 | | 4/2017 | Cookson et al. |
| 10,391,635 | B2 | | 8/2019 | Berghoefer et al. |
| 2010/0206120 | A1 | * | 8/2010 | Kinoshita ............ B25J 17/0283 901/29 |
| 2011/0071544 | A1 | * | 3/2011 | Steger ................ A61B 17/3498 606/130 |

(Continued)

FOREIGN PATENT DOCUMENTS

| | | |
|---|---|---|
| EP | 3179951 | 7/2021 |
| WO | WO 2011/060042 | 5/2011 |

OTHER PUBLICATIONS

International Search Report and Written Opinion for International (PCT) Patent Application No. PCT/IL2022/051222, dated Feb. 21, 2023, 16 pages.

*Primary Examiner* — Dale Moyer
(74) *Attorney, Agent, or Firm* — Sheridan Ross P.C.

(57) ABSTRACT

A robotic system according to at least one embodiment of the present disclosure includes a robot arm including a proximal end and a distal end, a mount flange rotationally connected to the robot arm at the distal end along a rotation axis, and an end effector interconnected to the mount flange via an attachment interface disposed between the mount flange and the end effector. The attachment interface fixedly arranges the end effector in one of at least two select positions. A first position of the at least two select positions orients a surgical tool axis of the end effector at a first angle relative to the rotation axis, and a second position of the at least two select positions orients the surgical tool axis of the end effector at a second angle relative to the rotation axis. The second angle is different from the first angle.

20 Claims, 9 Drawing Sheets

(56) References Cited

U.S. PATENT DOCUMENTS

| | | | |
|---|---|---|---|
| 2011/0094355 A1* | 4/2011 | Sheehy | B23B 29/205 82/159 |
| 2016/0045271 A1* | 2/2016 | McGrogan | A61B 34/30 901/38 |
| 2016/0167236 A1* | 6/2016 | Kato | B25J 15/0408 294/213 |
| 2017/0232618 A1* | 8/2017 | Pidan | G05B 19/19 700/164 |
| 2018/0311831 A1* | 11/2018 | Guerin | B25J 15/0483 |
| 2019/0231447 A1* | 8/2019 | Ebbitt | A61B 17/1622 |
| 2020/0276701 A1 | 9/2020 | Lii et al. | |
| 2020/0367873 A1* | 11/2020 | Troxell | A61B 17/0206 |
| 2020/0368898 A1 | 11/2020 | Perez | |
| 2021/0046657 A1* | 2/2021 | Safeldt | B25J 15/0441 |
| 2022/0039898 A1* | 2/2022 | Ding | A61B 46/10 |

* cited by examiner

MULTIPLE END EFFECTOR INTERFACES COUPLED WITH DIFFERENT KINEMATICS

BACKGROUND

The present disclosure is generally directed to surgical systems, and relates more particularly to robotic surgical devices.

Surgical robots may assist a surgeon or other medical provider in carrying out a surgical procedure, or may complete one or more surgical procedures autonomously. Providing controllable linked articulating members allows a surgical robot to reach areas of a patient anatomy during various medical procedures.

BRIEF SUMMARY

Example aspects of the present disclosure include:

A robotic system according to at least one embodiment of the present disclosure comprises: a robot arm comprising a proximal end and a distal end; a mount flange rotationally connected to the robot arm at the distal end along a rotation axis; and an end effector interconnected to the mount flange via an attachment interface disposed between the mount flange and the end effector, wherein the attachment interface fixedly arranges the end effector in one of at least two select positions, a first position of the at least two select positions orienting a surgical tool axis of the end effector at a first angle relative to the rotation axis, and a second position of the at least two select positions orienting the surgical tool axis of the end effector at a second angle relative to the rotation axis, wherein the second angle is different from the first angle.

Any of the aspects herein, wherein the second angle is disposed 90 degrees to the first angle. Any of the aspects herein, wherein the first position of the at least two select positions defines a first movement range and limit of the robotic system, wherein the second position of the at least two select positions defines a second movement range and limit of the robotic system, wherein the first movement range and limit is different from the second movement range and limit, and wherein a range of motion for a surgical tool mounted in the end effector in the first position is different from a range of motion for the surgical tool mounted in the end effector in the second position.

Any of the aspects herein, wherein the attachment interface corresponds to a kinematic mount disposed in the mount flange and corresponding kinematic mount contacts disposed in the end effector.

Any of the aspects herein, wherein the end effector further comprises: a tool block comprising a surgical tool receptacle passing from a first side of the tool block through a second side of the tool block, wherein the surgical tool axis coincides with an axis of the surgical tool receptacle, and wherein the tool block comprises the corresponding kinematic mount contacts.

Any of the aspects herein, wherein the kinematic mount disposed in the mount flange comprises: a first set of kinematic mounts arranged at the first angle; and a second set of kinematic mounts arranged at the second angle.

Any of the aspects herein, wherein the end effector is arranged in the first position of the at least two select positions when the corresponding kinematic mount contacts of the tool block are engaged with the first set of kinematic mounts arranged at the first angle.

Any of the aspects herein, wherein the end effector is arranged in the second position of the at least two select positions when the corresponding kinematic mount contacts of the tool block are engaged with the second set of kinematic mounts arranged at the second angle.

Any of the aspects herein, wherein the end effector comprises: a first tool block that arranges the end effector in the first position of the at least two select positions; and a second tool block that arranges the end effector in the second position of the at least two select positions.

Any of the aspects herein, wherein the attachment interface corresponds to a set of kinematic mounts disposed in the mount flange and corresponding kinematic mount contacts disposed in the first tool block and in the second tool block.

Any of the aspects herein, wherein the corresponding kinematic mount contacts disposed in the first tool block comprise a first set of kinematic mounts arranged at the first angle, wherein the corresponding kinematic mount contacts disposed in the first tool block comprise a second set of kinematic mounts arranged at the second angle, wherein the end effector is arranged in the first position of the at least two select positions when the first set of kinematic mounts of the first tool block are engaged with the kinematic mounts disposed in the mount flange, and wherein the end effector is arranged in the second position of the at least two select positions when the second set of kinematic mounts of the second tool block are engaged with the kinematic mounts disposed in the mount flange.

A robotic surgical system according to at least one embodiment of the present disclosure comprises: a robot arm comprising a plurality of links and joints arranged between a proximal end and a distal end of the robot arm; a distal end mount flange rotationally connected to a furthest link from the proximal end of the robot arm at a furthest joint from the proximal end of the robot arm, the distal end mount flange configured to rotate about a rotation axis of the furthest joint; and an end effector affixed to the distal end mount flange via a kinematic attachment interface disposed between the distal end mount flange and the end effector, wherein the kinematic attachment interface fixedly arranges the end effector in one of at least two positions relative to the distal end mount flange, a first position of the at least two positions orienting a surgical tool axis of the end effector at a first angle relative to the rotation axis, and a second position of the at least two positions orienting the surgical tool axis of the end effector at a second angle relative to the rotation axis, wherein the second angle is disposed orthogonal to the first angle.

Any of the aspects herein, wherein the first position defines a first movement range and limit of the plurality of links and joints of the robot arm including the end effector and a surgical tool affixed thereto, wherein the second position defines a second movement range and limit of the plurality of links and joints of the robot arm including the end effector and the surgical tool affixed thereto, and wherein the first movement range and limit provides a first set of positions for the surgical tool that are different from a second set of positions for the surgical tool associated with the second movement range and limit.

Any of the aspects herein, wherein, in the first position, the surgical tool axis of the end effector is arranged parallel to the rotation axis, and wherein, in the second position, the surgical tool axis of the end effector is arranged perpendicular to the rotation axis.

Any of the aspects herein, wherein the end effector further comprises: a surgical tool clamp block comprising a surgical tool receptacle passing from a first side of the surgical tool clamp block through a second side of the surgical tool clamp block, wherein the surgical tool axis coincides with an axis of the surgical tool receptacle, and wherein the tool block comprises at least one set of kinematic mount contacts.

Any of the aspects herein, wherein the at least one set of kinematic mount contacts comprises at least one spherical ball disposed in the surgical tool clamp block, tooling ball with post disposed in the surgical tool clamp block, and dowel pin disposed in the surgical tool clamp block.

Any of the aspects herein, wherein the distal end mount flange comprises: a set of kinematic mounts comprising at least one of a slot disposed in the distal end mount flange, a chamfered slot disposed in the distal end mount flange, a conical hole disposed in the distal end mount flange, a countersunk hole disposed in the distal end mount flange, a pair of parallel dowel pins separated from one another a distance and disposed in a slot of the distal end mount flange, and a counterbore disposed in the distal end mount flange, and wherein the set of kinematic mounts of the distal end mount flange kinematically interconnects with the at least one set of kinematic mount contacts of the end effector constraining the end effector to the distal end mount flange.

A system according to at least one embodiment of the present disclosure comprises: a surgical robot, comprising: a robot arm comprising a proximal end and a distal end; a mount flange rotationally connected to the robot arm at the distal end along a rotation axis; and an end effector interconnected to the mount flange via an attachment interface disposed between the mount flange and the end effector, wherein the attachment interface fixedly arranges the end effector in one attached position of at least two positions, a first position of the at least two positions orienting a surgical tool axis of the end effector at a first angle relative to the rotation axis, and a second position of the at least two positions orienting the surgical tool axis of the end effector at a second angle relative to the rotation axis, wherein the second angle is different from the first angle; and a processor coupled with the surgical robot; and a memory coupled with and readable by the processor and storing therein instructions that, when executed by the processor, cause the processor to: determine the one attached position of the end effector relative to the mount flange of the surgical robot; determine a movement profile for a surgical tool mounted to the end effector that is associated with the one attached position determined; and move the robot arm and the mount flange of the surgical robot according to the movement profile determined.

Any of the aspects herein, wherein the second angle is disposed 90 degrees to the first angle. Any of the aspects herein, wherein the wherein the end effector further comprises: a tool block comprising a surgical tool receptacle passing from a first side of the tool block through a second side of the tool block, wherein the surgical tool axis coincides with an axis of the surgical tool receptacle, and wherein the tool block mounts to the mount flange via a set of kinematic mount contacts.

Any of the aspects herein, wherein the tool block comprises an identification tag, and wherein the mount flange comprises an identification tag reader, and wherein, when the tool block is mounted to the mount flange, the identification tag aligns with the identification tag reader.

Any of the aspects herein, wherein, in determining the one attached position of the end effector relative to the mount flange and prior to determining the movement profile for the surgical tool, the instructions further cause the processor to: read, by the identification tag reader, an identification of the tool block stored in the identification tag; and retrieve, from the memory based on the identification of the tool block, axial arrangement information for the tool block defining a position of the surgical tool axis of the end effector relative to at least one of a surface of the tool block and the rotation axis.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one or more of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
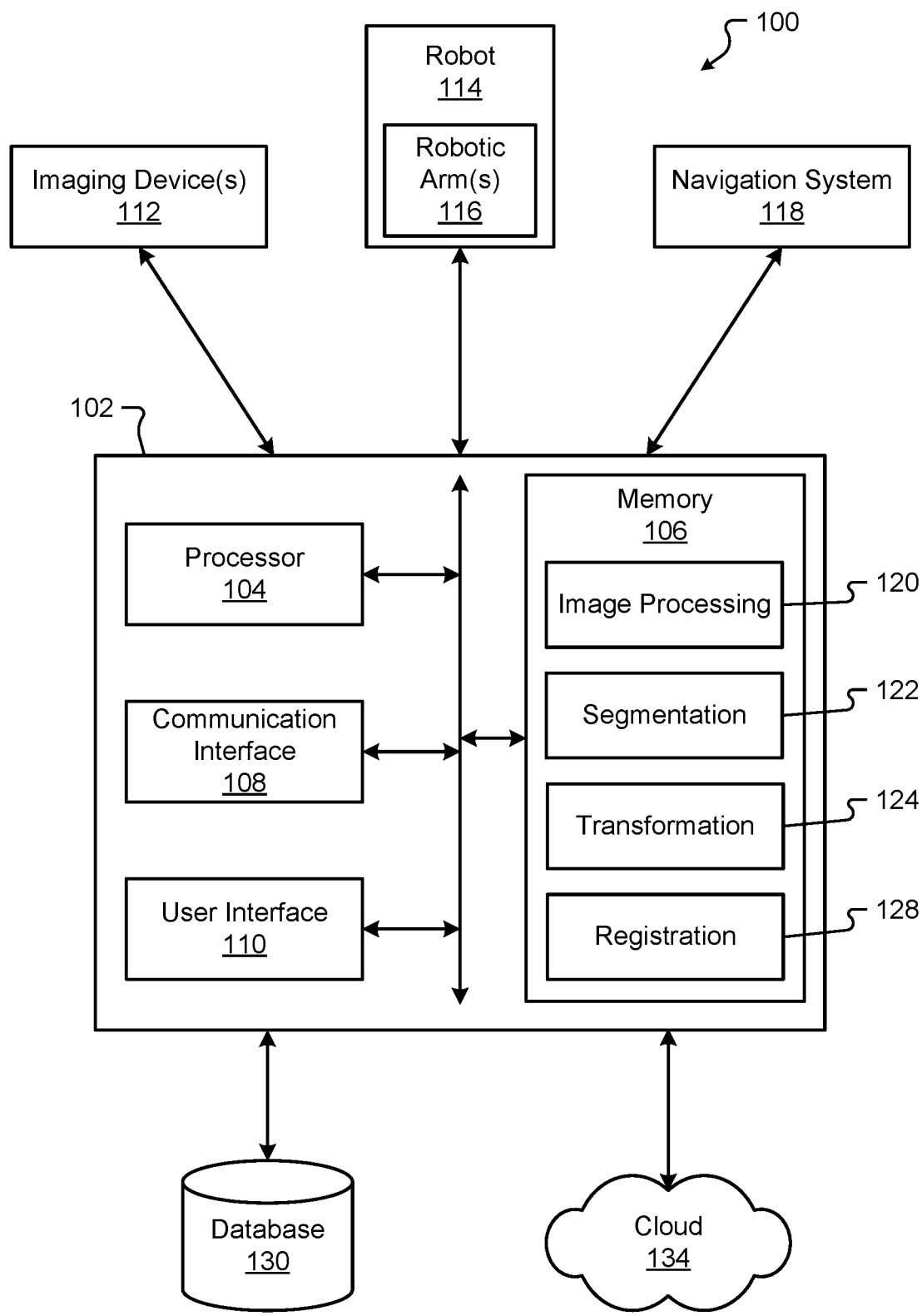
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Planning a single robot for various clinical applications raises a challenge as each application may have different requirements from the robot. For instance, one application may require maintaining the orientation of the tool the robot is holding but if that constraint is kept for a different application, for example, which does not require maintaining the tools orientation, the space of solutions for the second application may be reduced drastically. Embodiments of the present disclosure provide a solution for these challenges by, for example, including two separate interfaces between the robot's end effector and the applications end units that differ in 90 degrees from one to the other. In some examples, the separate interfaces between the robot's end effector and/or the end units may differ in any number of degrees from one another. Using this arrangement allows for two "different robots," each one with its own kinematic solutions (e.g., movement characteristics and capabilities, etc.) according to requirements of the application, to be created from a single robot.

In one example, the robot may comprise an end flange, or end effector mount flange, having a connection interface to which an end effector may be attached. The end effector may be mounted to the end effector mount flange in a first orientation or in a second orientation, for example, disposed at 90 degrees to the first orientation. The first orientation may arrange an axis of a surgical tool (e.g., of an end effector) to be disposed in a first movement position and the second orientation may arrange the axis of the surgical tool to be disposed in a second movement position. Between the first orientation and the second orientation the axis of the surgical tool may be shifted into a nonparallel and perpendicular axial position.

In a first interface of the end effector, the orientation of the tool may be maintained as one or more arms of the robot move. In a second interface of the end effector (e.g., where the tool axis is shifted 90 degrees from the first interface), the position of the tool may provide an extended space of solutions when the orientation of the tool is not maintained. The components of the robot may be the same but, in each case, the end effector is connected in a different orientation relative to the end effector mount flange. These different interfaces may allow each application to maintain the most important requirement (e.g., maintaining tool position, providing enhanced movement solutions, etc.). Each end effector connection interface will have a different set of kinematic solutions (e.g., movement capabilities and limits, etc.) for the robot. The end effector connection interface may comprise a number of attachment features (e.g., kinematic mount points, fasteners, etc.) disposed in the end effector mount flange and corresponding (e.g., mating) attachment features disposed in the tool block of the end effector.

In one example, the number of attachment features in the end effector mount flange may include a first set of features disposed at a first orientation and a second set of features arranged 90 degrees to the first set. In this case, a single tool block may include only one set of mating attachment features that, when mounted to the end effector mount flange, may be positioned in contact with the first set of features (e.g., arranging the tool in a first axial position relative to the robot) or in contact with the second set of features (e.g., arranging the tool in a second axial position relative to the robot, the second axial position being shifted 90 degrees relative to the first axial position). Although described as being shifted 90 degrees relative to the first axial position, it should be appreciated that the second axial position may be shifted by and number of degrees and the examples described herein are not limited to 90 degrees. For instance, the second axial position may be shifted any number of degrees between 0 degrees and 180 degrees.

In some examples, the number of attachment features in the end effector mount flange may include only one set of features disposed in a standard, or nonchanging, orientation. In this example, different tool blocks may be used to arrange an end effector and tool at a particular orientation relative to the end effector mount flange. For instance, a first tool block may include a first set of mating attachment features that interconnect with the set of features in the end effector mount flange and arrange a tool of the end effector in a first position. Continuing this example, a second tool block may include a second set of mating attachment features that interconnect with the set of features in the end effector mount flange and arrange the tool of the end effector in a second position that is shifted (e.g., 90 degrees) from the first position.

Embodiments of the present disclosure provide technical solutions to one or more of the problems of (1) using a single robot for a single application, (2) requiring complex change-over between robots depending on application, (3) limited movement capabilities that are unchangeable and associated with a particular robot, etc. In one example, the technical solutions may include broadening (e.g., increasing) the number of applications and capabilities of a single surgical robot without requiring multiple robotic systems or developing entire new robotic systems, and/or without requiring complex complete surgical robot changeover from one application to another. A robot comprising the multiple end effector attachments described herein may expand the range of movements available to a robot by rearranging and attaching an end effector at different mount positions and/or angles. The kinematics, or movement capabilities and limits, of the robot may be recalculated and/or selected based on the type of end effector and/or position of attachment detected providing a foolproof mechanical interchangeable system for the robot.

Turning first to FIG. 1, a block diagram of a system 100 according to at least one embodiment of the present disclosure is shown. The system 100 may be used to operate a robot 114 according to one of several defined movement paths or kinematic solutions associated with, and specific to, a connected end effector. In some examples, the system 100 may control, pose, and/or otherwise manipulate a surgical mount system, a surgical arm, and/or surgical tools attached thereto and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods described herein, or of any other methods. The memory 106 may store, for example, instructions and/or machine learning models that support one or more functions of the robot 114. For instance, the memory 106 may store content (e.g., instructions and/or machine learning models) that, when executed by the processor 104, enable image processing 120, segmentation 122, transformation 124, and/or registration 128. Such content, if provided as in instruction, may, in some embodiments, be organized into one or more applications, modules, packages, layers, or engines. Alternatively or additionally, the memory 106 may store other types of content or data (e.g., machine learning models, artificial neural networks, deep neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms 116 may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (e.g., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system 118 may comprise one or more electromagnetic sensors. In various embodiments, the navigation system 118 may be used to track a position and orientation (e.g., a pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The database 130 may store information that correlates one coordinate system to another (e.g., one or more robotic coordinate systems to a patient coordinate system and/or to a navigation coordinate system). The database 130 may additionally or alternatively store, for example, one or more surgical plans (including, for example, pose information about a target and/or image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; and/or any other useful information. In one example, the database 130 may comprise movement profiles for the robot 114 based on a select end effector that is attached to the robotic arm 116. These movement profiles may correspond to kinematic solutions for the robot 114 and/or defined positions of a surgical tool axis of select end effector relative to at least one of a surface of a tool block of the end effector and a rotation axis of a final joint/mount flange of the robotic arm 116. In some examples, the database 130 may store identifications of specific tool blocks and surgical tool axis orientations. In any event, the database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the methods (e.g., method 700, etc.) described herein. The system 100 or similar systems may also be used for other purposes.

Figure 2A:
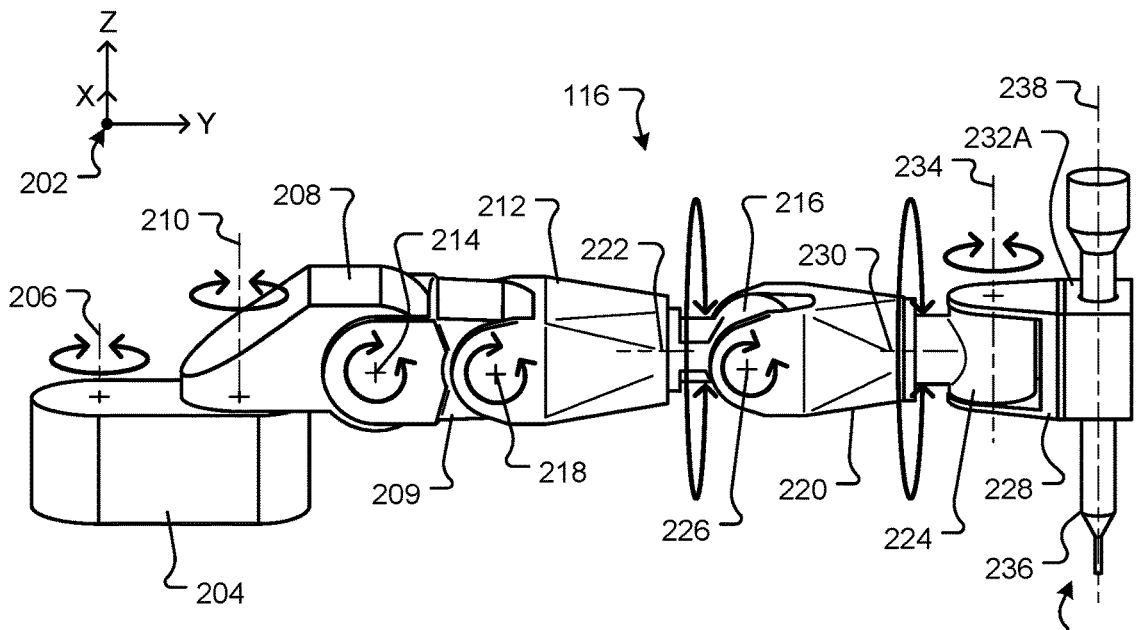
FIG. 2A is a perspective diagram of a robotic surgical system and end effector having first movement kinematics according to at least one embodiment of the present disclosure.
Figure 2B:
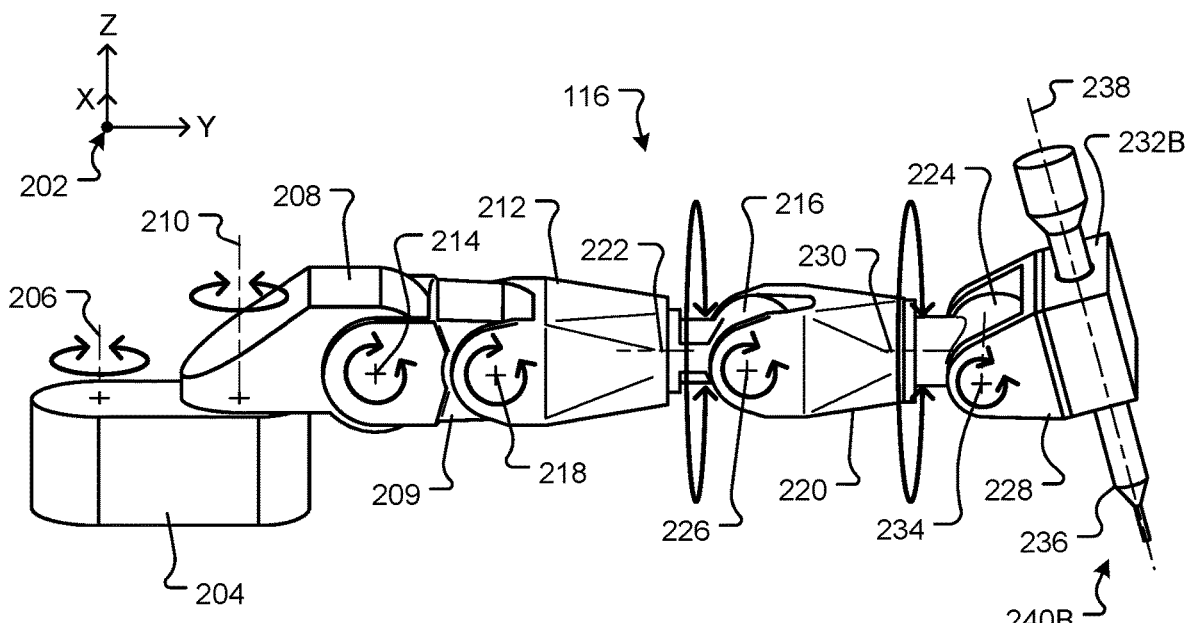
FIG. 2B is a perspective diagram of a robotic surgical system and end effector having second movement kinematics according to at least one embodiment of the present disclosure.

Referring now to FIGS. 2A and 2B, perspective diagrams of a robotic surgical system with different end effector 240A, 240B mount positions are shown in accordance with examples of the present disclosure. More specifically, FIGS. 2A and 2B show the robotic arm 116 of the robot 114 connected to an end effector 240A, 240B holding a surgical tool 236. While shown as a single surgical tool 236 in FIGS. 2A and 2B, the surgical tool 236 may correspond to different surgical tools used between operations in a surgical application. For instance, a first surgical tool 236 may include a direction-specific blade that may require a specific rotational alignment and placement in the tool block 232A, 232B, while another surgical tool 236 may include a unidirectional cutting tool that is independent of rotational alignment in the tool block 232A, 232B.

Features of the robot 114 and/or robotic arm 116 may be described in conjunction with a coordinate system 202. The coordinate system 202, as shown in FIGS. 2A and 2B, includes three-dimensions comprising an X-axis, a Y-axis, and a Z-axis. Additionally or alternatively, the coordinate system 202 may be used to define planes (e.g., the XY-plane, the XZ-plane, and the YZ-plane) of the robot 114 and/or robotic arm 116. These planes may be disposed orthogonal, or at 90 degrees, to one another. While the origin of the coordinate system 202 may be placed at any point on or near the components of the robot 114, for the purposes of description, the axes of the coordinate system 202 are always disposed along the same directions from figure to figure, whether the coordinate system 202 is shown or not. In some examples, reference may be made to dimensions, angles, directions, relative positions, and/or movements associated with one or more components of the robot 114 and/or robotic arm 116 with respect to the coordinate system 202. For example, the width of the robotic arm 116 (e.g., running from the side shown in the foreground to the side in the background, into the page) may be defined as a dimension along the X-axis of the coordinate system 202, the height of the robotic arm 116 may be defined as a dimension along the Z-axis of the coordinate system 202, and the length of the robotic arm 116 (e.g., running from a proximal end at the first link 204 to a distal end at the seventh link 224, etc.) may be defined as a dimension along the Y-axis of the coordinate system 202. Additionally or alternatively, the height of the system 100 may be defined as a dimension along the Z-axis of the coordinate system 202, a reach of the robotic arm 116 may be defined as a dimension along the Y-axis of the coordinate system 202, and a working area of the robotic arm 116 may be defined in the XY-plane with reference to the corresponding axes of the coordinate system 202.

The robotic arm 116 may be comprised of a number of links 204, 208, 209, 212, 216, 220, 224 that interconnect with one another at respective axes of rotation 206, 210, 214, 218, 222, 226, 230, 234, or joints. There may be more or fewer links 204, 208, 209, 212, 216, 220, 224 and/or axes of rotation 206, 210, 214, 218, 222, 226, 230, 234 than are shown in FIGS. 2A and 2B. In any event, the robotic arm 116 may have a first link 204 disposed at a proximal end of the robotic arm 116 and an end mount flange 228 disposed furthest from the proximal end at a distal end of the robotic arm 116. The first link 204 may correspond to a base of the robotic arm 116. In some examples, the first link 204 may rotate about first rotation axis 206. A second link 208 may be connected to the first link 204 at a second rotation axis 210, or joint. The second link 208 may rotate about the second rotation axis 210. In one example, the first rotation axis 206 and the second rotation axis 210 may be arranged parallel to one another. For instance, the first rotation axis 206 and the second rotation axis 210 are shown extending along the Z-axis in a direction perpendicular to the XY-plane.

The robotic arm 116 may comprise a third link 209 that is rotationally interconnected to the second link 208 via the third rotation axis 214, or joint. The third rotation axis 214 is shown extending along the X-axis, or perpendicular to the first rotation axis 206 and second rotation axis 210. In this position, when the third link 209 is caused to move (e.g., rotate relative to the second link 208), the third link 209 (and the components of the robotic arm 116 extending from the third link 209) may be caused to move into or out of the XY-plane. The fourth link 212 is shown rotationally interconnected to the third link 209 via the fourth rotation axis 218, or joint. The fourth rotation axis 218 is arranged parallel to the third rotation axis 214. The fourth rotation axis 218 extends along the X-axis allowing rotation of the fourth link 212 into and out of the XY-plane.

In some examples, the robotic arm 116 may comprise one or more wrists 216, 224. The fifth link 216, or wrist, is shown rotationally interconnected to the fourth link 212 via a fifth rotation axis 222, or wrist joint. The fifth rotation axis 222 is shown extending along the Y-axis, which is perpendicular to the X-axis and the Z-axis. During operation of the robot 114, causing the fifth link 216 to rotate about the fifth rotation axis 222 may cause the components of the robotic arm 116 distal the joint at the fifth rotation axis 222 (e.g., the fifth link 216, the sixth link 220, the seventh link 224, the end mount flange 228, and the end effector 240A, 240B, etc.) to rotate about the Y-axis.

The sixth link 220 is rotationally interconnected to the fifth link 216 via the sixth rotation axis 226. The sixth rotation axis 226 extends along the X-axis and provides for rotation of the sixth link 220 relative to the fifth link 216 (e.g., into and out of the XY-plane in the position shown).

The seventh link 224, or wrist, is shown rotationally interconnected to the sixth link 220 via a seventh rotation axis 230, or wrist joint. The seventh rotation axis 230 is shown extending along the Y-axis (e.g., perpendicular to the X-axis and the Z-axis). During operation of the robot 114, causing the seventh link 224 to rotate about the seventh rotation axis 230 may cause the components of the robotic arm 116 distal the joint at the seventh rotation axis 230 (e.g., the end mount flange 228, and the end effector 240A, 240B, etc.) to rotate about the Y-axis.

Located at the distal end of the robotic arm 116, an end mount flange 228 may be rotationally interconnected to the end mount flange 228 via an eighth, or mount flange rotation, axis 234. In FIG. 2A, the seventh link 224 is positioned rotationally about the seventh rotation axis 230 such that the end mount flange 228 is oriented where the mount flange rotation axis 234 is extending along the Z-axis. In FIG. 2B, the seventh link 224 is positioned rotationally about the seventh rotation axis 230 such that the end mount flange 228 is oriented where the mount flange rotation axis 234 is extending along the X-axis. It is an aspect of the present disclosure that at least the seventh link 224 may be rotated about the seventh rotation axis 230 to move between the end mount flange 228 position shown in FIG. 2A and the end mount flange 228 position shown in FIG. 2B, or vice versa. The end mount flange 228 and the mount flange rotation axis 234 may be the last movable (e.g., motor actuated, etc.) link and joint of the robotic arm 116. Moving between these two positions of the end mount flange 228 allows a particular end effector 240A, 240B to be attached and manipulated, or operated, according to a corresponding movement profile (e.g., range and limits) or set of kinematic solutions for the robot 114 (e.g., the robotic arm 116 and the surgical tool 236, etc.).

FIG. 2A shows first movement kinematics for the robotic arm 116 when the first tool block 232A of the first end effector 240A disposes the surgical tool axis 238 parallel to the mount flange rotation axis 234. In the position shown in FIG. 2A, rotation into and/or out of the XY-plane between the seventh link 224 and the first end effector 240A is prevented. This position and arrangement may be ideal for applications (e.g., operations, procedures, etc.) where an end rotational position of the surgical tool 236 may need to be maintained for the robotic arm 116. For example, the surgical tool 236 in the first end effector 240A may correspond to an imaging device that may need to be maintained in a particular nonrotational position relative to a patient during imaging (e.g., where an imaging plane of the surgical tool 236 should be maintained parallel to the XY-plane as other joints of the robotic arm 116 move the distal end closer to or further from the proximal end). In this case, the corresponding arrangement of the surgical tool axis 238 (e.g., parallel to the mount flange rotation axis 234) associated with the first end effector 240A may be preferred. In another example, rotation of the surgical tool 236 into, or out of, the XY-plane may need to be prevented to ensure accuracy of movement along the Y-axis, in the XY-plane, and/or the like. Additionally or alternatively, a distance between a reference plane and an end of the surgical tool 236 (e.g., along the Z-axis) may need to remain constant during operation of the robot 114. In any of these cases, the position and arrangement shown in conjunction with FIG. 2A (e.g., preventing end rotation relative to the XY-plane) may be preferred.

FIG. 2B shows second movement kinematics for the robotic arm 116 when the second tool block 232B of the second end effector 240B disposes the surgical tool axis 238 perpendicular (e.g., at 90 degrees) to the mount flange rotation axis 234. In this alternative position, the end mount flange 228 and second end effector 240B may be allowed to rotate relative to the seventh link 224. Stated another way, in this alternative position, the end mount flange 228 and second end effector 240B may be allowed to rotate into and/or out of the XY-plane (e.g., relative to seventh link 224 at the mount flange rotation axis 234). This position and arrangement may be ideal when a precise rotational movement of the surgical tool 236 at the distal end of the robotic arm 116 is desired. In contrast to the position and arrangement shown in FIG. 2A, where the closest rotation of the first end effector 240A about the X-axis is provided at the sixth rotation axis 226, the position and arrangement of FIG. 2B allows the second end effector 240B to be rotated about the X-axis about the mount flange rotation axis 234. Among other things, this position and arrangement may be used for any application where a movement of the second end effector 240B including an end rotation into and/or out of the XY-plane is desired for the surgical tool 236. Such applications may include directional cutting operations, probing movements, displacement of tissue and organs, and/or other surgical operations.

Figure 3B:
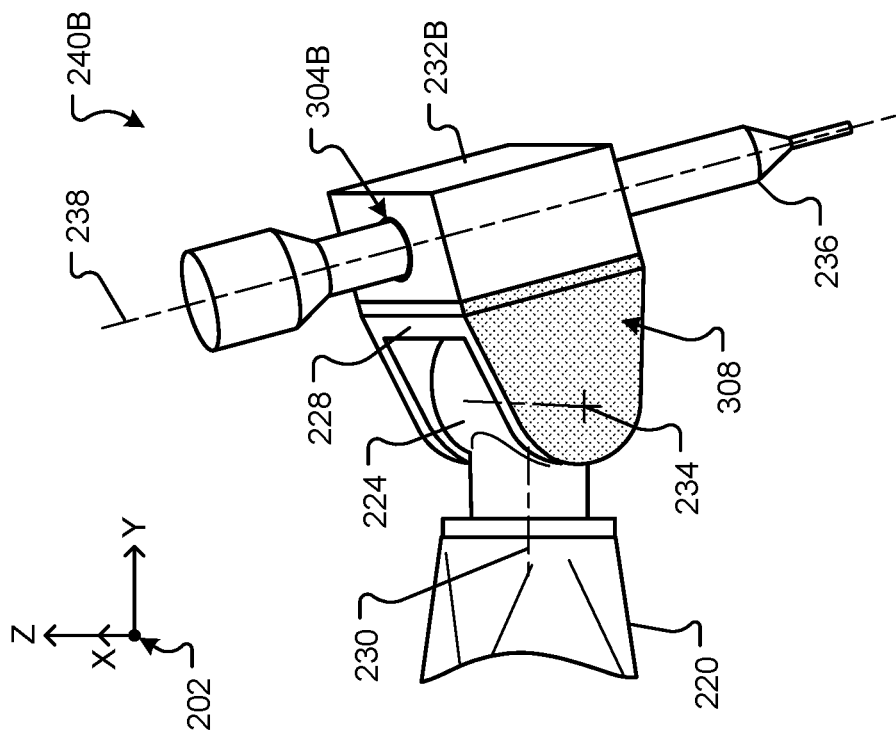
FIG. 3B is a detail perspective view of an end effector portion of a robotic surgical system having the second movement kinematics according to at least one embodiment of the present disclosure.
Figure 3A:
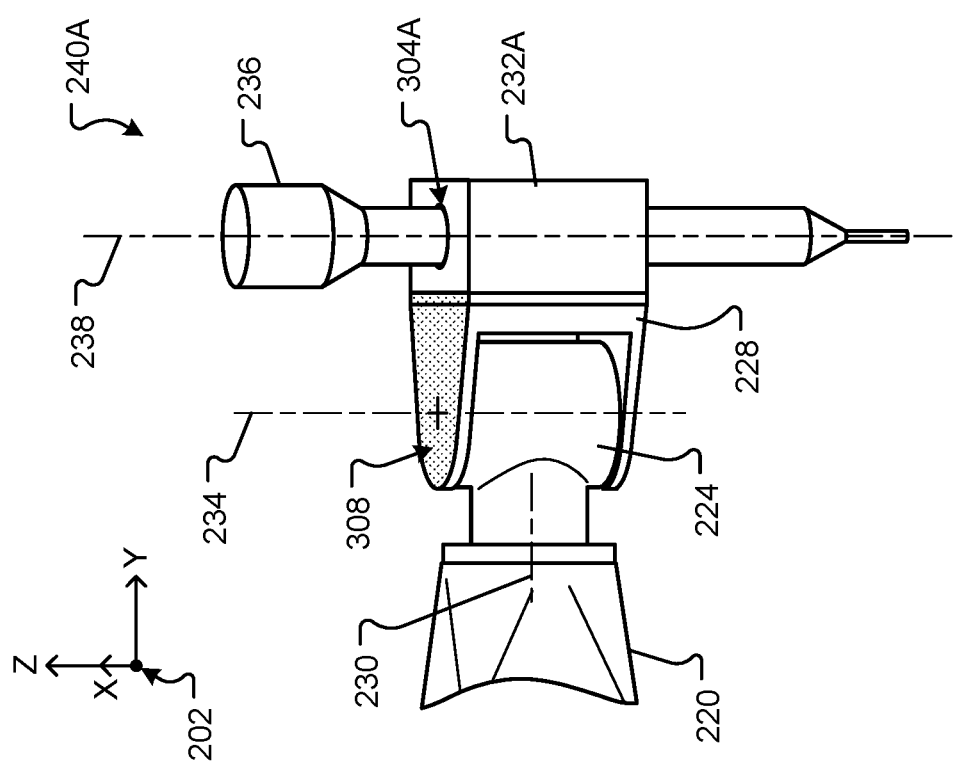
FIG. 3A is a detail perspective view of an end effector portion of a robotic surgical system having the first movement kinematics according to at least one embodiment of the present disclosure.

FIGS. 3A and 3B show detail perspective views of the distal end (e.g., the end effector portion) of the robotic arm 116 with the first end effector 240A attached and the second end effector 240B attached, respectively. As illustrated in FIG. 3A, the first end effector 240A may comprise a first tool block 232A having a first surgical tool receptacle 304A disposed therein. The first surgical tool receptacle 304A may define a surgical tool axis 238 of the first tool block 232A. In one example, an axis of the first surgical tool receptacle 304A may coincide with a surgical tool axis 238. When attached to the end mount flange 228, the first tool block 232A disposes the surgical tool axis 238 parallel to the mount flange rotation axis 234. As shown in FIG. 3A, the reference surface 308 of the end mount flange 228 is disposed parallel to the XY-plane facing up. When in the position and arrangement shown in FIGS. 2A and 3A, the first end effector 240A comprises first movement kinematics (e.g., ranges and limits) for the robotic arm 116 and the surgical tool 236.

FIG. 3B shows an alternative position and arrangement of the surgical tool 236 relative to the end mount flange 228. As shown in FIG. 3B, the end mount flange 228 is oriented such that the reference surface 308 is now disposed parallel to the YZ-plane facing forward. It is an aspect of the present disclosure that the first end effector 240A may be removed from the end mount flange 228 and the position and arrangement shown in FIG. 3A, and second end effector 240B may be attached to the end mount flange 228 providing the alternative position and arrangement shown in FIG. 3B. The alternative position and arrangement of FIG. 3B provides second movement kinematics for the robotic arm 116 and the surgical tool 236. If the first end effector 240A was not removed and the end mount flange 228 was rotated from the position shown in FIG. 3A to the position shown in FIG. 3B, the surgical tool axis 238 would extend along the X-axis. However, by repositioning the second end effector 240B such that the surgical tool axis 238 is in the YZ-plane, different movement characteristics are provided for the robotic arm 116 and surgical tool 236. As described herein the end effectors 240A, 240B may comprise different tool blocks 232A, 232B (e.g., having a unique arrangement of surgical tool receptacles 304A, 304B, etc.) or may correspond to an end effector 240A, 240B comprising a same tool block 232A, 232B only oriented at 90 degrees between the position and arrangement shown in FIGS. 3A and 3B. Various combinations of options for the end effectors 240A, 240B are shown and described in conjunction with FIGS. 4-6B.

Figure 4:
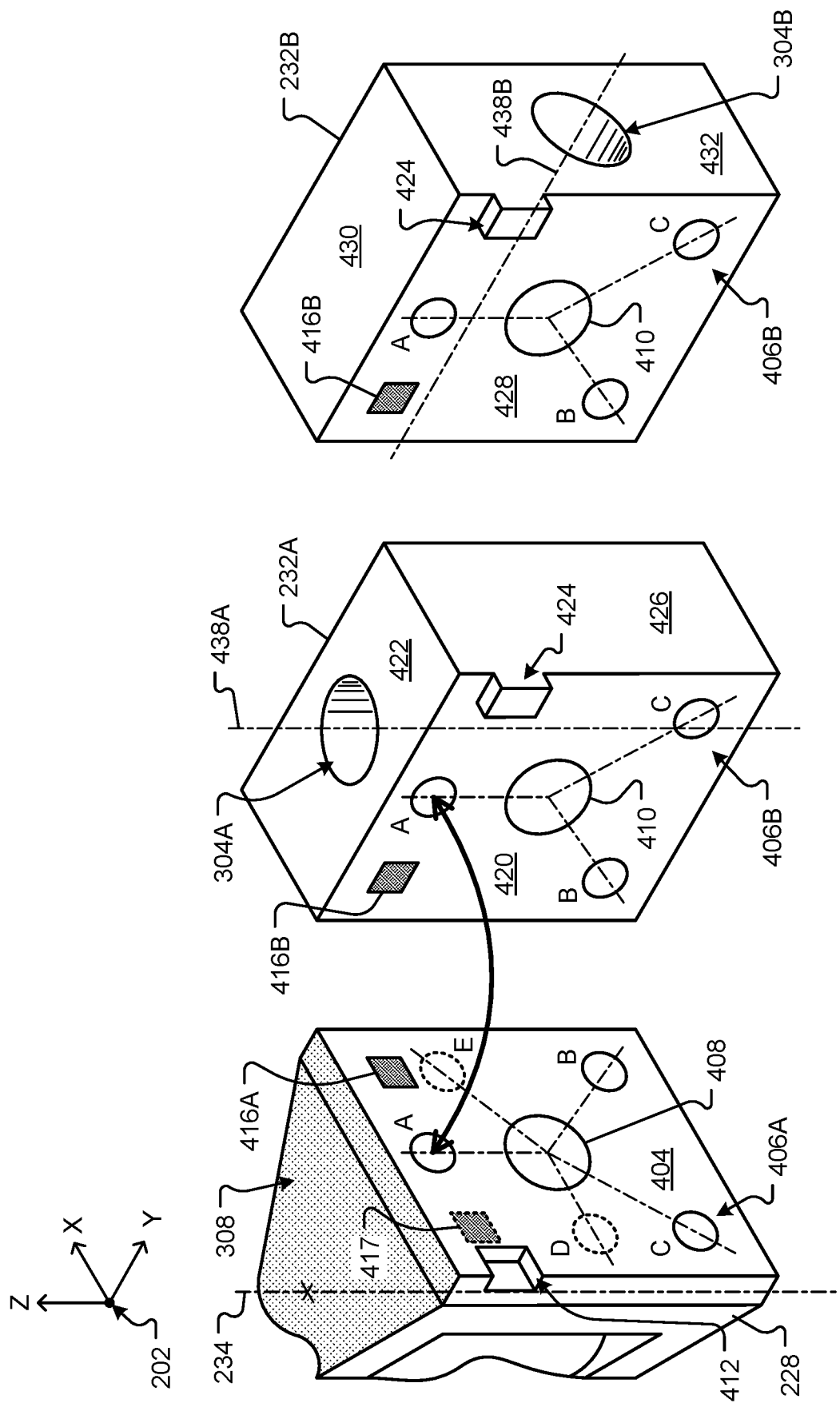
FIG. 4 is a perspective view of a robot end effector mount flange and tool blocks according to at least one embodiment of the present disclosure.

FIG. 4 is a perspective view of an end mount flange 228 and separated tool blocks 232A, 232B according to embodiments of the present disclosure. The end mount flange 228 is shown to include a flange mount surface 404 and a number of kinematic mounts 406A disposed therein. The kinematic mounts 406A may correspond to one or more kinematic mounts including, but in no way limited to, chamfered slots, conical recesses, countersunk holes, counterbores, parallel dowel pins disposed in a slot offset a distance from one another, hardened slots, and/or combinations thereof. The kinematic mounts 406A may be arranged in a set. For example, a first set of the kinematic mounts 406A may comprise mounts located at positions A, B, and C on the flange mount surface 404 (e.g., set {A, B, C}). In one example, these locations may be separated from one another by 120 degrees (e.g., taken about a center of the first magnetic block 408). In some examples, a second set of the kinematic mounts 406A may comprise mounts located at positions D, E, and B (e.g., set {D, E, C}). The second set of the kinematic mounts 406A may provide an interface that is rotated 90 degrees relative to the first set of the kinematic mounts 406A (e.g., 90 degrees counterclockwise about the center of the first magnetic block 408, about the Y-axis, etc.).

The arrangement of the kinematic mounts 406A (e.g., relative to on another in a set) may match corresponding kinematic mount contacts 406B that are disposed in the first tool block 232A and/or second tool block 232B. The kinematic mount contacts 406B may correspond to one or more contacts including, but in no way limited to, spherical balls, tooling balls with posts, dowel pins, and/or other protrusions that extend from the first block mount surface 420 and/or second block mount surface 428. When the first tool block 232A or the second tool block 232B is attached to the end mount flange 228 such that the flange mount surface 404 of the end mount flange 228 is arranged adjacent and facing the first block mount surface 420 or the second block mount surface 428, respectively, the kinematic mount contacts 406B contact and mate with the respective kinematic mounts 406A in the flange mount surface 404. For instance, when attached, the kinematic mount contact at position A, of the kinematic mount contacts 406B, contacts the kinematic mounts at position A of the kinematic mounts 406A. Continuing this example, the kinematic mount contact at position B, of the kinematic mount contacts 406B, contacts the kinematic mounts at position B of the kinematic mounts 406A. In some examples, the kinematic mount contact at position C, of the kinematic mount contacts 406B, contacts the kinematic mounts at position C of the kinematic mounts 406A.

The first tool block 232A or the second tool block 232B may be held in contact with the end mount flange 228 via a fastener (e.g., a screw, a bolt, etc.) and/or via a magnetic interface (e.g., a magnetic attraction provided by one or more magnets). For example, the first magnetic block 408 and/or the second magnetic block 410 may correspond to a magnet (e.g., a rare earth magnet, permanent magnets, an electromagnet, etc.) and/or a ferrous material that is attracted to an applied magnetic field. Examples of permanent magnets may include, but are in no way limited to, neodymium (e.g., neodymium-iron-boron), samarium-cobalt, ferrite, aluminum-nickel-cobalt, combinations thereof, and/or the like. In some examples, the first magnetic block 408 and the second magnetic block 410 may both be magnets. In this example, the magnets may be arranged such that opposite poles face each other when the end mount flange 228 and the first tool block 232A or second tool block 232B are attached. For instance, the first magnetic block 408 shown in FIG. 4 may dispose a north pole adjacent the flange mount surface 404 while the second magnetic block 410 may dispose a south pole adjacent the first block mount surface 420 or the second block mount surface 428. In this arrangement, a maximum magnetic force may be maintained between the magnetic blocks 408, 410 ensuring the end mount flange 228 and the first tool block 232A or the second tool block 232B are fixedly connected, and kinematically constrained, to one another.

When two separate tool blocks 232A, 232B are used to shift the position of the surgical tool axis 238 relative to the mount flange rotation axis 234, each tool block 232A, 232B may comprise an orientation protrusion 424 that keys and/or engages with a corresponding orientation recess 412 disposed in the end mount flange 228, or vice versa. At least one benefit to using such a keyed feature provides quick location and connection, prevents misaligned tool blocks 232A, 232B, and ensures proper engagement between the tool blocks 232A, 232B and the end mount flange 228. As shown in FIG. 4, the first tool block 232A comprises a first surgical tool receptacle 304A extending from a first top surface 422 through the body of the first tool block 232A. When the first tool block 232A is attached to the end mount flange 228, the first surgical tool axis 438A (corresponding to the surgical tool axis 238) is arranged parallel to the mount flange rotation axis 234. In contrast, the second tool block 232B comprises a second surgical tool receptacle 304B extending from a second side surface 432 through the body of the second tool block 232B. When the second tool block 232B is attached to the end mount flange 228, the second surgical tool axis 438B (corresponding to the surgical tool axis 238) is arranged perpendicular (e.g., at 90 degrees) to the mount flange rotation axis 234.

At least one identification tag reader 416A, 417 may be mounted to the end mount flange 228. The identification tag reader 416A, 417 may correspond to a radio frequency identification (RFID) tag reader. The tool blocks 232A, 232B may each comprise at least one identification tag 416B. The identification tag 416B may correspond to an RFID tag. The identification tag 416B may comprise an identification of the tool block 232A, 232B to which it is attached, information about the axial arrangement of the surgical tool receptacle 304A, 304B for the tool block 232A, 232B, and/or other information about the tool block 232A, 232B or surgical tool 236 that is compatible with the tool block 232A, 232B. In some examples, the information stored in the identification tag 416B may be read by the identification tag reader 416A, 417 and, in response, the robot 114 may determine an appropriate registration, kinematic calculations, movement and limit data, and/or other operational data for the robot 114.

In some examples, the kinematic mounts 406A of the end mount flange 228 may include a first set (e.g., set {A, B, C}) and a 90-degree shifted second set (e.g., set {D, E, B}) of mounts. In this example, only one of the tool blocks 232A, 232B would need to be used to provide two different axial orientations of the surgical tool axis 238 relative to the mount flange rotation axis 234. For instance, the first tool block 232A may be used to attach to the end mount flange 228 in a first position (e.g., where kinematic mount contacts 406B in set {A, B, C} mate with kinematic mounts 406A in set {A, B, C}, respectively) and in an alternative second position (e.g., where kinematic mount contacts 406B in set {A, B, C} mate with kinematic mounts 406A in set {D, E, B}), shifting the first surgical tool axis 438A from being parallel with the mount flange rotation axis 234 to being perpendicular with the mount flange rotation axis 234. In this example, when the first tool block 232A is in the first position the identification tag reader 416A aligns with the identification tag 416B and when the first tool block 232A is moved to the second position, the alternative mount position identification tag reader 417 aligns with the identification tag 416B. The methods described herein may determine an axial arrangement of the first surgical tool axis 438A based on which identification tag reader 416A, 417 detected the identification tag 416B of the first tool block 232A. In this example, the orientation protrusion 424 and orientation recess 412 interface may not be required and can be removed. Although described above as utilizing the first tool block 232A as a universal clamp block for the surgical tool 236 (e.g., a block that can orient the surgical tool axis 238 parallel to the mount flange rotation axis 234 or perpendicular to the mount flange rotation axis 234, it should be appreciated that the second tool block 232B may be utilized in a similar manner as described.

Figure 5A:
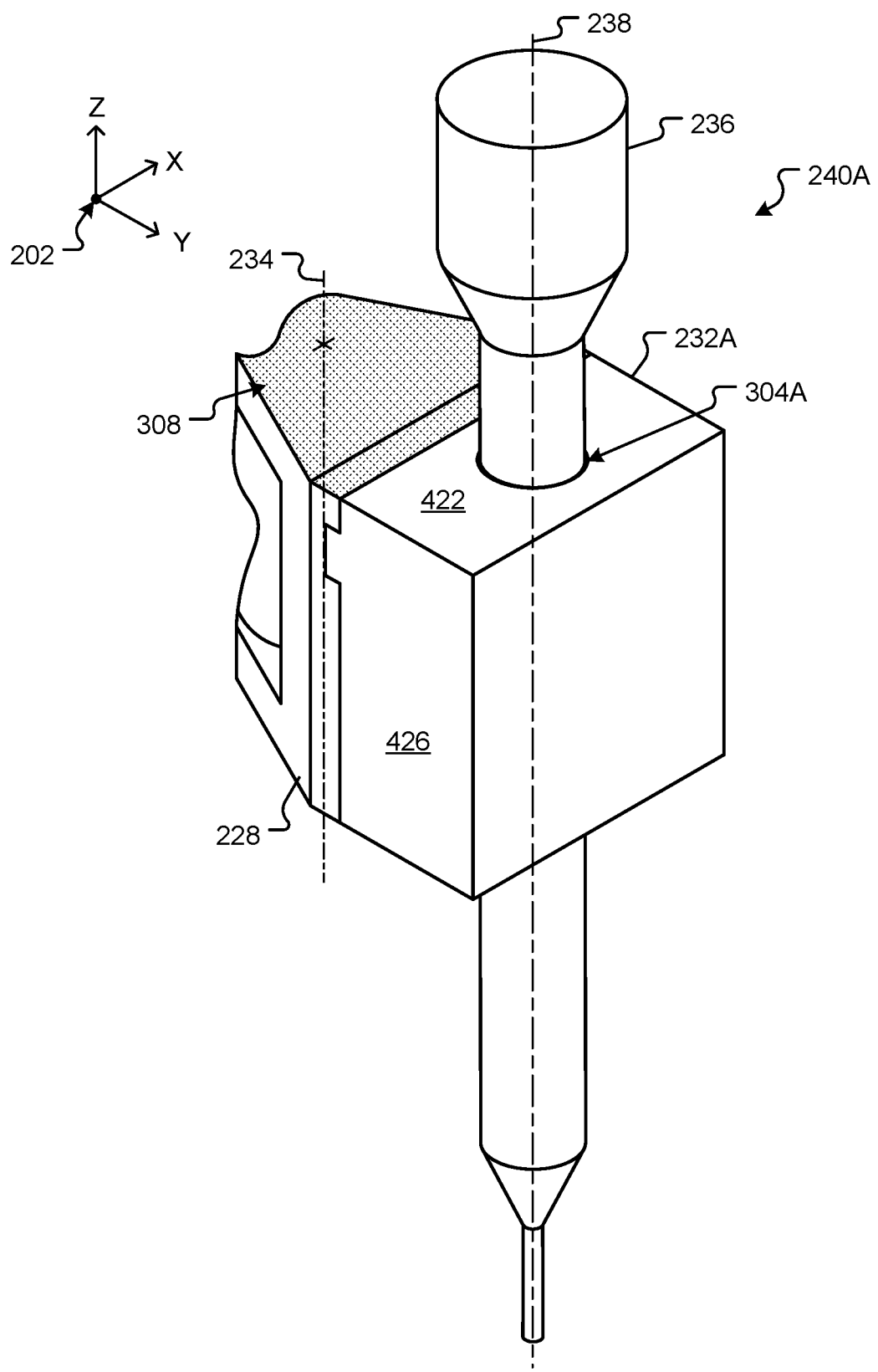
FIG. 5A is a detail perspective view of a robot end effector providing the first movement kinematics according to at least one embodiment of the present disclosure.
Figure 5B:
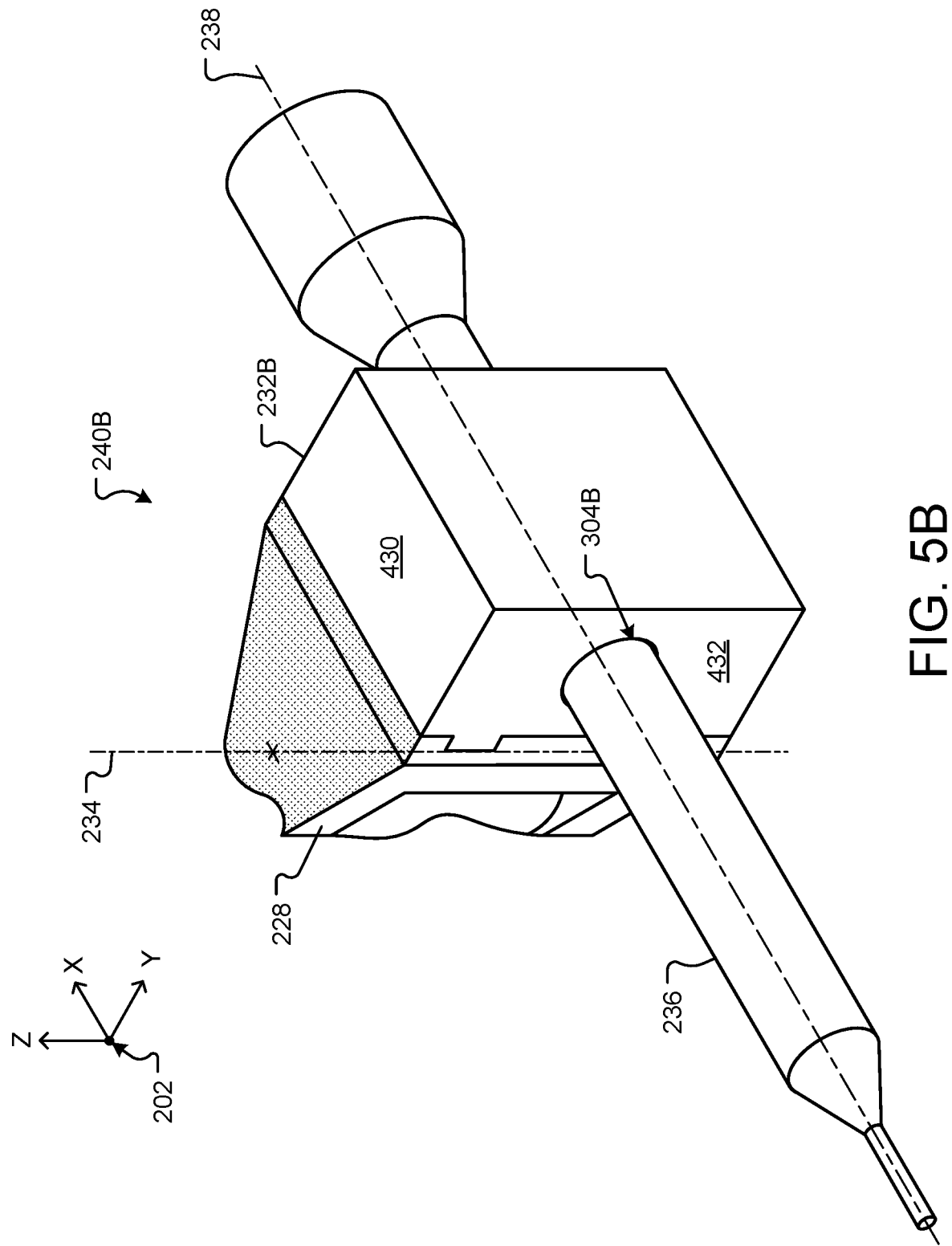
FIG. 5B is a detail perspective view of a robot end effector providing the second movement kinematics according to at least one embodiment of the present disclosure.

FIGS. 5A and 5B show detail perspective views of the distal end of the robotic arm 116 and, more specifically, the end effectors 240A, 240B comprising different tool blocks 232A, 232B arranging the surgical tool axis 238 in different positions relative to the mount flange rotation axis 234. This kinematic mount interface provides a connection between a single set of kinematic mounts 406A of end mount flange 228 and a single set of kinematic mount contacts 406B on a respective tool block 232A, 232B. As illustrated in FIG. 4, the kinematic mount contacts 406B between the first tool block 232A and the second tool block 232B are shifted 90 degrees relative to the axis of a respective surgical tool receptacle 304A, 304B.

In FIG. 5A, the first end effector 240A comprises the first tool block 232A, where the first surgical tool receptacle 304A passes from the first top surface 422 through the body of the first tool block 232A (in a direction along the Z-axis). As shown in FIG. 5A, the surgical tool axis 238 is disposed parallel to the mount flange rotation axis 234 providing first movement kinematics (e.g., movement ranges, limits, capabilities, etc.) for the robotic arm 116 and the surgical tool 236. The arrangement shown in FIG. 5A may correspond to the first end effector 240A shown in FIGS. 2A and 3A, or vice versa.

In FIG. 5B, the second end effector 240B comprises the second tool block 232B, where the second surgical tool receptacle 304B passes from the second side surface 432 through the body of the second tool block 232B (in a direction along the X-axis). The surgical tool axis 238 shown in FIG. 5B is disposed perpendicular to the mount flange rotation axis 234 providing second movement kinematics (e.g., movement ranges, limits, capabilities, etc.) for the robotic arm 116 and the surgical tool 236. The arrangement shown in FIG. 5B may correspond to the second end effector 240B shown in FIGS. 2B and 3B, or vice versa.

As provided above, the end mount flange 228 may comprise multiple sets of kinematic mounts 406A that are arranged to receive at least one of the tool blocks 232A, 232B in multiple axial orientations. These sets of kinematic mounts 406A may be shifted rotationally about the Y-axis relative one another, as shown in FIG. 4. Although FIG. 4 shows at least one shared kinematic mount (e.g., mount B) between sets of kinematic mounts 406A, embodiments of the present disclosure are not so limited. For instance, the sets of kinematic mounts 406A may share more or fewer kinematic mounts 406A than illustrated in FIG. 4. An example of the kinematic mount interface between the end mount flange 228 and the end effectors 240A, 240B utilizing a single re-mountable (e.g., rotated 90 degrees between mount points) tool block 232A, 232B, is shown in FIGS. 6A and 6B.

Figure 6A:
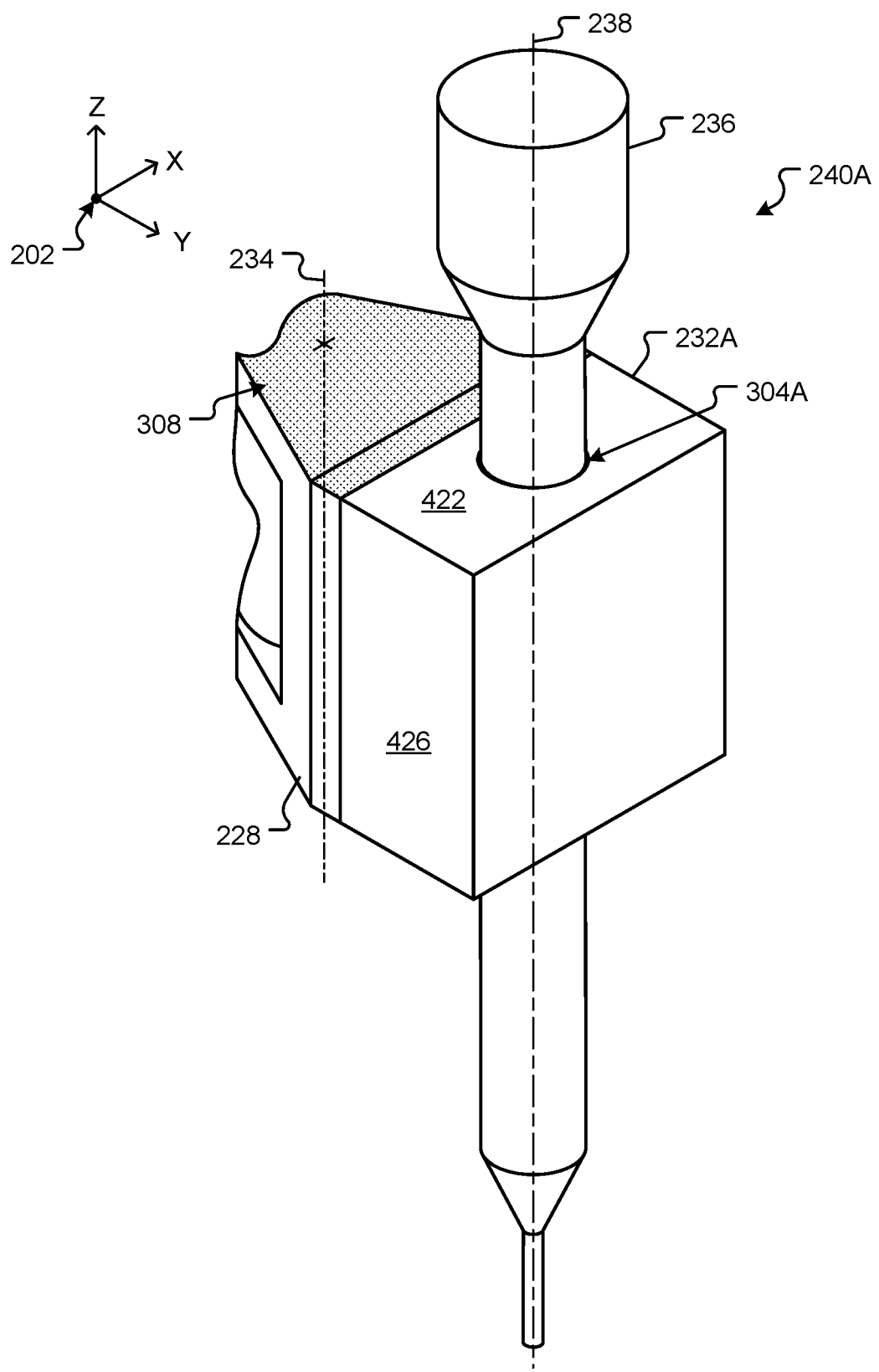
FIG. 6A is a detail perspective view of a robot end effector providing the first movement kinematics according to at least one embodiment of the present disclosure.
Figure 6B:
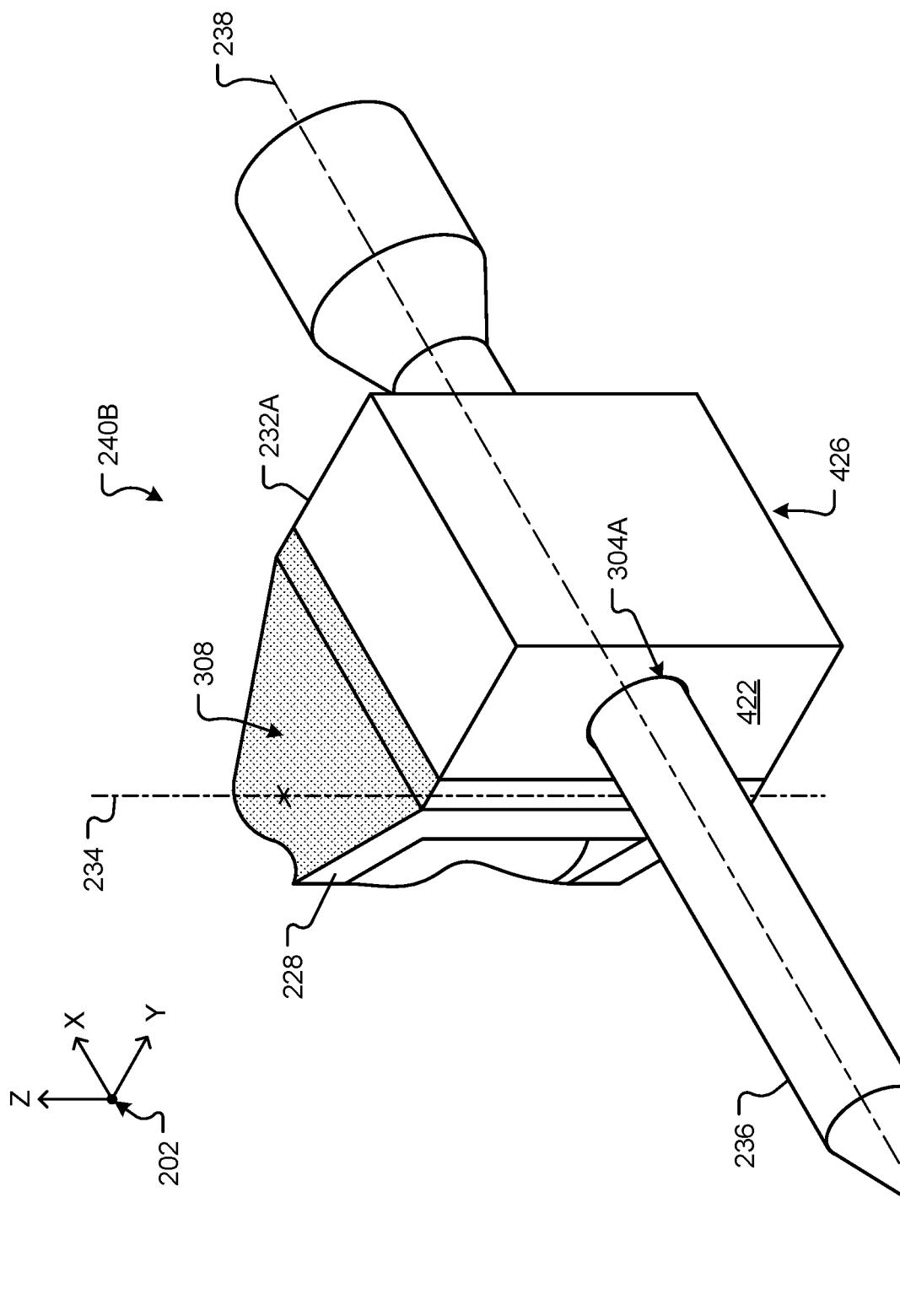
FIG. 6B is a detail perspective view of a robot end effector providing the second movement kinematics according to at least one embodiment of the present disclosure.

In FIGS. 6A and 6B, a single tool block 232A, 232B is attached to the end mount flange 228 in different positions to arrange the surgical tool axis 238 relative to the mount flange rotation axis 234 in specific orientations (e.g., providing different movement kinematics for the robotic arm 116 and surgical tool 236). For the sake of example, the first tool block 232A is attached to the end mount flange 228 in a first position in FIG. 6A. In this first position, the kinematic mount contacts 406B in set {A, B, C} of the first tool block 232A mate with kinematic mounts 406A in set {A, B, C} of the end mount flange 228 (see, e.g., FIG. 4). As shown in FIG. 6A, the surgical tool axis 238 is disposed parallel to the mount flange rotation axis 234 providing first movement kinematics (e.g., movement ranges, limits, capabilities, etc.) for the robotic arm 116 and the surgical tool 236. The arrangement shown in FIG. 6A may correspond to the first end effector 240A shown in FIGS. 2A and 3A, or vice versa.

In FIG. 6B, the first tool block 232A is attached to the end mount flange 228 in a second position. In this second position, the kinematic mount contacts 406B in set {A, B, C} of the first tool block 232A mate with kinematic mounts 406A in the 90-degree shifted set {D, E, B} of the end mount flange 228 (see, e.g., FIG. 4). In one example, the first tool block 232A may be removed from the end mount flange 228 in the first position shown in FIG. 6A and then reattached to the end mount flange 228 in the second position shown in FIG. 6B, or vice versa. As shown in FIG. 6B, the surgical tool axis 238 is disposed perpendicular to the mount flange rotation axis 234 providing second movement kinematics (e.g., movement ranges, limits, capabilities, etc.) for the robotic arm 116 and the surgical tool 236. The arrangement shown in FIG. 6B may correspond to the second end effector 240B shown in FIGS. 2B and 3B, or vice versa.

Figure 7:
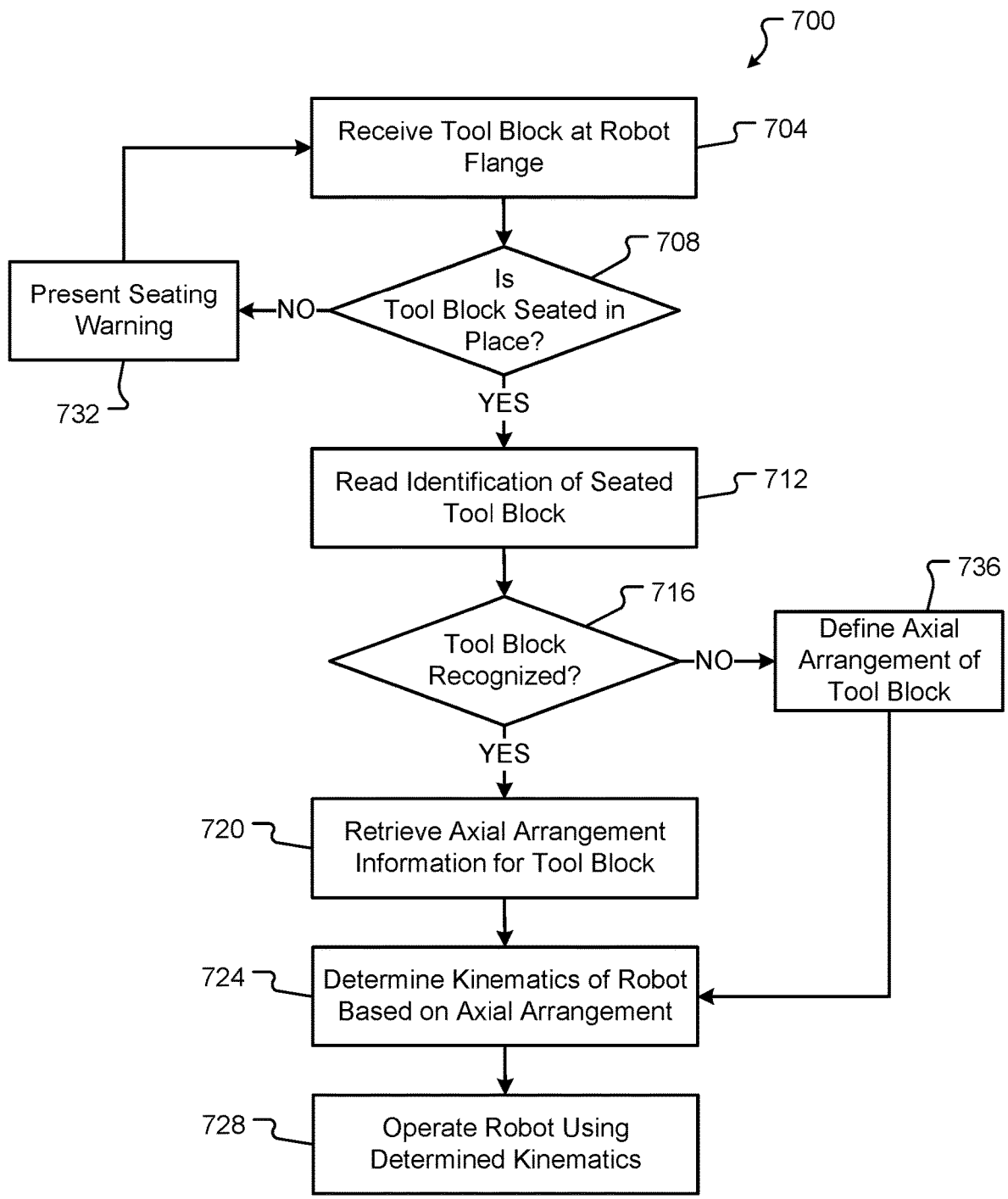
FIG. 7 is a flowchart of a method for operating a robotic surgical system based on determined movement kinematics for a mounted end effector according to at least one embodiment of the present disclosure.

FIG. 7 depicts a method 700 that may be used, for example, in operating the robot 114 and/or one or more portions of the robotic arm 116 based on determined movement kinematics for a mounted end effector 240A, 240B.

The method 700 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 700. The at least one processor may perform the method 700 by executing elements stored in a memory such as the memory 106. The elements stored in the memory and executed by the processor may cause the processor to execute one or more steps of a function as shown in method 700. One or more portions of a method 700 may be performed by the processor executing any of the contents of memory, such as transformation 124 and/or registration 128 instructions.

The method 700 may begin by receiving a tool block 232A, 232B at the end mount flange 228 located at the distal end of the robotic arm 116 (step 704). The proximal end of the robotic arm 116 may be associated with a base or a base link (e.g., first link 204) and the distal end of the robotic arm 116 may correspond to a working end of the robotic arm 116. In some examples, receiving the tool block 232A, 232B may comprise selecting a particular tool block 232A, 232B and aligning the kinematic mount contacts 406B with corresponding kinematic mounts 406A on the end mount flange 228.

In one example, the first tool block 232A and/or the end mount flange 228 may include one or more features that ensures proper kinematic interface engagement and/or alignment. For instance, the end mount flange 228 may comprise an orientation recess 412, protrusion, key, slot, pin, or other feature that receives an orientation protrusion 424, slot, keyway, pin, and/or hole of the tool block 232A, 232B. The method 700 may proceed by determining whether the tool block 232A, 232B is properly seated in place with the end mount flange 228 (step 708). When a tool block 232A, 232B is rotated out of position such that the orientation protrusion 424 (or other orientation feature) does not engage with the orientation recess 412 (or other corresponding orientation feature) of the end mount flange 228, the method 700 may proceed to step 732 by presenting a "seating warning" to the user interface 110 (step 732). The warning may be made based on a misalignment of the identification tag reader 416A and the identification tag 416B, a Hall effect sensor indicating that the orientation recess 412 and the orientation protrusion 424 are misaligned, and/or some other alignment sensor ensuring proper alignment between the tool block 232A, 232B and the end mount flange 228. In some examples, the warning may be based on the processor 104 determining that the identification tag reader 416A is unable to read the identification tag 416B. In any event, the warning may be rendered to a display device and include information regarding the improper seating of the tool block 232A, 232B.

When the tool block 232A, 232B is properly engaged with the end mount flange 228, the method 700 may proceed by the identification tag reader 416A, 417 reading the identification tag 416B of the tool block 232A, 232B (step 712). In some examples, the identification tag reader 416A, 417 may read the identification tag 416B when the identification tag reader 416A, 417 and the identification tag 416B are brought into proximity to one another (e.g., when the end effector 240A, 240B is attached to the end mount flange 228). The identification tag 416B may correspond to an RFID tag, near field communication (NFC) tag, and/or the like. The identification tag 416B may include information about the type of tool block 232A, 232B, an axial location of the surgical tool axis 238 of the tool block 232A, 232B, one or more surgical tool 236 that are compatible with the tool block 232A, 232B and/or other information.

Next, the method 700 may proceed by determining whether the tool block 232A, 232B is recognized (step 716). Recognition may correspond to the processor 104 determining whether the information from the identification tag 416B is associated with a known type of tool block 232A, 232B or end effector 240A, 240B and an associated axial alignment of the surgical tool axis 238. This step may include the processor 104 referring to data stored in the identification tag 416B, the memory 106, the database 130, and/or the cloud 134. For example, the processor 104 may retrieve an identification of the tool block 232A, 232B from the identification tag 416B and then, using the identification, look up a corresponding or associated data record stored in the memory 106, the database 130, and/or the cloud 134 for a match.

In the event that the tool block 232A, 232B is not recognized, the method 700 may proceed to step 736 where the axial arrangement of the end effector 240A, 240B and/or the tool block 232A, 232B may be defined. For instance, a user may assign an axial arrangement for the surgical tool axis 238 of the end effector 240A, 240B based on an orientation of the surgical tool axis 238 with the mount flange rotation axis 234 of the robotic arm 116. This defined axial arrangement may be stored in the identification tag 416B and/or in the memory 106, the database 130, and/or the cloud 134 by the processor 104.

When the tool block 232A, 232B is recognized, the processor 104 may refer to one or more of the identification tag 416B, the memory 106, the database 130, and/or the cloud 134 for axial arrangement information for the tool block 232A, 232B (step 720). The axial arrangement information may indicate an orientation of the surgical tool axis 238 of the tool block 232A, 232B relative to the kinematic mount contacts 406B, at least one surface of the tool block 232A, 232B, and/or the mount flange rotation axis 234 of the robotic arm 116.

Based on the axial arrangement, the processor 104 may determine movement kinematics for the robot 114 (e.g., the robotic arm 116, the end effector 240A, 240B, and the surgical tool 236)(step 724). The movement kinematics may define a movement range and limits of the surgical tool 236 when the end effector 240A, 240B is mounted to the end mount flange 228 of the robotic arm 116 according to the associated axial arrangement. For instance, the movement kinematics when the surgical tool axis 238 is parallel to the mount flange rotation axis 234 are different from the movement kinematics when the surgical tool axis 238 is perpendicular to the mount flange rotation axis 234. When the axial arrangement is such that the surgical tool axis 238 is disposed parallel to the mount flange rotation axis 234, the movement kinematics may be the same as those described in conjunction with FIGS. 2A, 3A, 5A, and 6A (e.g., first movement kinematics). When the axial arrangement is such that the surgical tool axis 238 is disposed perpendicular to the mount flange rotation axis 234, the movement kinematics may be the same as those described in conjunction with FIGS. 2B, 3B, 5B, and 6B.

The method 700 may proceed by operating the robot 114 based on the determined kinematics that are associated with the axial arrangement (step 728). Operating the robot 114 may comprise moving one or more links 204, 208, 209, 212, 216, 220, 224 and axes of rotation 206, 210, 214, 218, 222, 226, 230, 234, or joints, of the robotic arm 116 causing a movement of the surgical tool 236 held in the end effector 240A, 240B. For example, the robotic arm 116 and the end mount flange 228 may be moved according to the kinematic solutions available for the axial arrangement of the surgical tool axis 238 relative to the last joint (e.g., the mount flange rotation axis 234). The tool block 232A, 232B may be removed and reattached to the end mount flange 228 such that the surgical tool axis 238 is oriented in a different position (e.g., shifted 90 degrees) to allow movement of the robot 114 according to different kinematic solutions. Among other things, the ability to change the surgical tool axis 238 of an end effector 240A, 240B relative to the mount flange rotation axis 234 provides for an enhanced range of movement solutions (e.g., capabilities, ranges, limits, etc.) that would otherwise be unavailable for a robot having an end effector with only one axial arrangement relative to the last movable joint.

The present disclosure encompasses embodiments of the method 700 that comprise more or fewer steps than those described above, and/or one or more steps that are different than the steps described above.

As noted above, the present disclosure encompasses methods with fewer than all of the steps identified in FIG. 7 (and the corresponding description of the method 700), as well as methods that include additional steps beyond those identified in FIG. 7 (and the corresponding description of the method 700). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A robotic system, comprising:
   a robot arm comprising a proximal end and a distal end;
   a mount flange rotationally connected to the robot arm at the distal end along a rotation axis; and
   an end effector interconnected to the mount flange via an attachment interface disposed between the mount flange and the end effector, wherein the attachment interface fixedly arranges the end effector in one of at least two select positions, a first position of the at least two select positions orienting a surgical tool axis of the end effector at a first angle relative to the rotation axis, and a second position of the at least two select positions orienting the surgical tool axis of the end effector at a second angle relative to the rotation axis, wherein the second angle is different from the first angle, wherein, in the first position, the surgical tool axis of the end effector is arranged parallel to the rotation axis such that the surgical tool axis of the end effector and the rotation axis are arranged in a common plane together, and wherein, in the second position, the surgical tool axis of the end effector is arranged perpendicular to the rotation axis such that the surgical tool axis of the end effector and the rotation axis are not arranged in the common plane together.

2. The robotic system of claim 1, wherein the first position of the at least two select positions defines a first movement range and limit of the robotic system, wherein the second position of the at least two select positions defines a second movement range and limit of the robotic system, wherein the first movement range and limit is different from the second movement range and limit, and wherein a range of motion for a surgical tool mounted in the end effector in the first position is different from a range of motion for the surgical tool mounted in the end effector in the second position.

3. The robotic system of claim 2, wherein the attachment interface corresponds to a kinematic mount disposed in the mount flange and corresponding kinematic mount contacts disposed in the end effector.

4. The robotic system of claim 3, wherein the end effector further comprises:
   a tool block comprising a surgical tool receptacle passing from a first side of the tool block through a second side of the tool block, wherein the surgical tool axis coincides with an axis of the surgical tool receptacle, and wherein the tool block comprises the corresponding kinematic mount contacts.

5. The robotic system of claim 4, wherein the kinematic mount disposed in the mount flange comprises:
   a first set of kinematic mounts arranged at the first angle; and
   a second set of kinematic mounts arranged at the second angle.

6. The robotic system of claim 5, wherein the end effector is arranged in the first position of the at least two select positions when the corresponding kinematic mount contacts of the tool block are engaged with the first set of kinematic mounts arranged at the first angle.

7. The robotic system of claim 5, wherein the end effector is arranged in the second position of the at least two select positions when the corresponding kinematic mount contacts of the tool block are engaged with the second set of kinematic mounts arranged at the second angle.

8. The robotic system of claim 1, wherein the end effector comprises:
   a first tool block that arranges the end effector in the first position of the at least two select positions; and
   a second tool block that arranges the end effector in the second position of the at least two select positions.

9. The robotic system of claim 8, wherein the attachment interface corresponds to a set of kinematic mounts disposed in the mount flange and corresponding kinematic mount contacts disposed in the first tool block and in the second tool block.

10. The robotic system of claim 9, wherein the corresponding kinematic mount contacts disposed in the first tool block comprise a first set of kinematic mounts arranged at the first angle, wherein the corresponding kinematic mount contacts disposed in the first tool block comprise a second set of kinematic mounts arranged at the second angle, wherein the end effector is arranged in the first position of the at least two select positions when the first set of kinematic mounts of the first tool block are engaged with the set of kinematic mounts disposed in the mount flange, and wherein the end effector is arranged in the second position of the at least two select positions when the second set of kinematic mounts of the second tool block are engaged with the set of kinematic mounts disposed in the mount flange.

11. A robotic surgical system, comprising:
    a robot arm comprising a plurality of links and joints arranged between a proximal end and a distal end of the robot arm;
    a distal end mount flange rotationally connected to a furthest link from the proximal end of the robot arm at a furthest joint from the proximal end of the robot arm, the distal end mount flange configured to rotate about a rotation axis of the furthest joint; and
    an end effector affixed to the distal end mount flange via a kinematic attachment interface disposed between the distal end mount flange and the end effector, wherein the kinematic attachment interface fixedly arranges the end effector in one of at least two positions relative to the distal end mount flange, a first position of the at least two positions orienting a surgical tool axis of the end effector at a first angle relative to the rotation axis, and a second position of the at least two positions orienting the surgical tool axis of the end effector at a second angle relative to the rotation axis, wherein, in the first position, the surgical tool axis of the end effector is arranged parallel to the rotation axis such that the surgical tool axis of the end effector and the rotation axis are arranged in a common plane together, and wherein, in the second position, the surgical tool axis of the end effector is arranged perpendicular to the rotation axis such that the surgical tool axis of the end effector and the rotation axis are not arranged in the common plane together.

12. The robotic surgical system of claim 11, wherein the first position defines a first movement range and limit of the plurality of links and joints of the robot arm including the end effector and a surgical tool affixed thereto, wherein the second position defines a second movement range and limit of the plurality of links and joints of the robot arm including the end effector and the surgical tool affixed thereto, and wherein the first movement range and limit provides a first set of positions for the surgical tool that are different from a second set of positions for the surgical tool associated with the second movement range and limit.

13. The robotic surgical system of claim 12, wherein the end effector further comprises:

a surgical tool clamp block comprising a surgical tool receptacle passing from a first side of the surgical tool clamp block through a second side of the surgical tool clamp block, wherein the surgical tool axis coincides with an axis of the surgical tool receptacle, and wherein the surgical tool clamp block comprises at least one set of kinematic mount contacts.

14. The robotic surgical system of claim 13, wherein the at least one set of kinematic mount contacts comprises at least one spherical ball disposed in the surgical tool clamp block, tooling ball with post disposed in the surgical tool clamp block, and dowel pin disposed in the surgical tool clamp block.

15. The robotic surgical system of claim 13, wherein the distal end mount flange comprises:
a set of kinematic mounts comprising at least one of a slot disposed in the distal end mount flange, a chamfered slot disposed in the distal end mount flange, a conical hole disposed in the distal end mount flange, a countersunk hole disposed in the distal end mount flange, a pair of parallel dowel pins separated from one another a distance and disposed in a slot of the distal end mount flange, and a counterbore disposed in the distal end mount flange, and wherein the set of kinematic mounts of the distal end mount flange kinematically interconnects with the at least one set of kinematic mount contacts of the end effector constraining the end effector to the distal end mount flange.

16. A system, comprising:
a surgical robot, comprising:
a robot arm comprising a proximal end and a distal end;
a mount flange rotationally connected to the robot arm at the distal end along a rotation axis; and
an end effector interconnected to the mount flange via an attachment interface disposed between the mount flange and the end effector, wherein the attachment interface fixedly arranges the end effector in one attached position of at least two positions, a first position of the at least two positions orienting a surgical tool axis of the end effector at a first angle relative to the rotation axis, and a second position of the at least two positions orienting the surgical tool axis of the end effector at a second angle relative to the rotation axis, wherein the second angle is different from the first angle, wherein, in the first position, the surgical tool axis of the end effector is arranged parallel to the rotation axis such that the surgical tool axis of the end effector and the rotation axis are arranged in a common plane together, and wherein, in the second position, the surgical tool axis of the end effector is arranged perpendicular to the rotation axis such that the surgical tool axis of the end effector and the rotation axis are not arranged in the common plane together;
a processor coupled with the surgical robot; and
a memory coupled with and readable by the processor and storing therein instructions that, when executed by the processor, cause the processor to:
determine the one attached position of the end effector relative to the mount flange of the surgical robot;
determine a movement profile for a surgical tool mounted to the end effector that is associated with the one attached position determined; and
move the robot arm and the mount flange of the surgical robot according to the movement profile determined.

17. The system of claim 16, wherein the end effector further comprises:
a tool block comprising a surgical tool receptacle passing from a first side of the tool block through a second side of the tool block, wherein the surgical tool axis coincides with an axis of the surgical tool receptacle, and wherein the tool block mounts to the mount flange via a set of kinematic mount contacts.

18. The system of claim 17, wherein the tool block comprises an identification tag, and wherein the mount flange comprises an identification tag reader, and wherein, when the tool block is mounted to the mount flange, the identification tag aligns with the identification tag reader.

19. The system of claim 18, wherein, in determining the one attached position of the end effector relative to the mount flange and prior to determining the movement profile for the surgical tool, the instructions further cause the processor to:
read, by the identification tag reader, an identification of the tool block stored in the identification tag; and
retrieve, from the memory based on the identification of the tool block, axial arrangement information for the tool block defining a position of the surgical tool axis of the end effector relative to at least one of a surface of the tool block and the rotation axis.

20. The system of claim 16, wherein the surgical robot further comprises:
a link arranged at the distal end of the robot arm proximal to the mount flange, wherein the mount flange is rotationally connected to the link along the rotation axis, wherein the link is rotational about a link axis that is arranged in a fixed perpendicular arrangement to the rotation axis, wherein, in the first position, the link is arranged in a first rotational position relative to a reference plane of the surgical robot such that the rotation axis is arranged perpendicular to the reference plane of the surgical robot, wherein, in the second position, the link is arranged in a second rotational position relative to the reference plane of the surgical robot such that rotation axis is arranged parallel to the reference plane of the surgical robot, wherein, in the first position, a rotation of the mount flange and end effector into the reference plane is prevented, and wherein, in the second position, the rotation of the mount flange and end effector into the reference plane is allowed.

* * * * *